United States Patent [19]

Seshimoto et al.

[11] Patent Number: 5,122,969
[45] Date of Patent: Jun. 16, 1992

[54] BIOCHEMICAL ANALYSIS APPARATUS, METHOD FOR CORRECTING THE RESULTS OF BIOCHEMICAL ANALYSES, AND CORRECTION VALUE RECORDING MEDIUM FOR THE SAME

[75] Inventors: Osamu Seshimoto; Masao Kitajima, both of Saitama, Japan

[73] Assignee: Fuji Photo Film Co., Ltd., Kanagawa, Japan

[21] Appl. No.: 480,466

[22] Filed: Feb. 15, 1990

[30] Foreign Application Priority Data

Feb. 17, 1989 [JP] Japan .................. 1-37738

[51] Int. Cl.$^5$ ............................................. G06F 15/02
[52] U.S. Cl. ............................ 364/497; 364/571.01; 364/571.04; 364/571.08; 235/462
[58] Field of Search ............... 364/497, 498, 571.01, 364/571.04, 571.08; 73/1 G, 863.03, 863, 864.21; 422/64, 65, 67, 56, 57; 204/146, 412; 235/462; 436/43, 47

[56] References Cited

U.S. PATENT DOCUMENTS

| | | | |
|---|---|---|---|
| 3,960,497 | 6/1976 | Acord | 364/571.01 |
| 3,992,158 | 11/1976 | Przybylowicz et al. | 422/57 |
| 4,043,756 | 8/1977 | Sommervold | 364/571.04 |
| 4,053,381 | 10/1977 | Hamblen et al. | 204/146 |
| 4,158,545 | 6/1979 | Yamashita et al. | 364/497 |
| 4,292,272 | 9/1981 | Kitajima et al. | 422/57 |
| 4,337,222 | 6/1982 | Kitajima et al. | 422/56 |
| 4,338,279 | 7/1982 | Orima et al. | 364/497 |
| 4,437,970 | 3/1984 | Kitajima et al. | 204/412 |
| 4,472,505 | 9/1984 | Manabe et al. | 364/498 |
| 4,587,102 | 5/1986 | Nagatomo et al. | 422/56 |
| 4,935,875 | 6/1990 | Shah et al. | 235/462 |

FOREIGN PATENT DOCUMENTS

| | | |
|---|---|---|
| 051183 | 10/1981 | European Pat. Off. |
| 0212612 | 8/1986 | European Pat. Off. |
| 0247439 | 5/1987 | European Pat. Off. |

*Primary Examiner*—Thomas G. Black
*Assistant Examiner*—Ellis B. Ramirez
*Attorney, Agent, or Firm*—Sughrue, Mion, Zinn, Macpeak & Seas

[57] ABSTRACT

A biochemical analysis apparatus comprises a movement device which moves analysis media containing a reagent or an electrochemical sensor, which will interact with a specific biochemical substance contained in liquid samples and give rise to changes in the analysis media, along a movement path connecting an introducing section and an ejecting section. While the analysis media are present in the movement path, a measurement device measures changes which have occurred in analysis media. A reading device reads information about correction values, which are to be used in order to correct a calibration curve so that it becomes suitable for analysis media used in analyses, from a correction value recording medium. A correction device corrects the calibration curve on the basis of the correction values. An operation device uses the corrected calibration curve in order to determine the concentration or the activity of the specific biochemical substance in a liquid sample from the value measured by the measurement device.

7 Claims, 7 Drawing Sheets

BIOCHEMICAL ANALYSIS APPARATUS, METHOD FOR CORRECTING THE RESULTS OF BIOCHEMICAL ANALYSES, AND CORRECTION VALUE RECORDING MEDIUM FOR THE SAME

BACKGROUND OF THE INVENTION

1. Field of the Invention

This invention relates to a method for correcting the results of biochemical analyses. This invention particularly relates to a method for correcting the results of biochemical analyses wherein errors in the analyses or a variation in values obtained from the analyses, which errors or variation are caused by a difference in characteristics between a plurality of groups of analysis media, are eliminated. Typical reasons for such errors or variation are a difference in characteristics between production lots of analysis media, and a difference in characteristics between groups (for example, packaging units) of analysis media, which have been stored for different periods. The biochemical analyses are carried out with analysis media containing a color forming reagent, which will chemically react with a specific biochemical substance contained in liquid samples, such as blood or urine, and give rise to a change in optical density, or with analysis media containing an electrochemical sensor which will electrochemically react with the biochemical substance and give rise to a change in current or potential. In the biochemical analyses, the liquid samples are independently applied to the analysis media, and changes in optical density or changes in current or potential, which changes have occurred in the analysis media, are measured. Thereafter, a calibration curve, which represents the relationship between the changes in optical density, or the changes in current or potential, and the concentrations or the activities of the biochemical substance in the liquid samples, is used in order to determine the concentrations or the activities of the biochemical substance from the measured changes in optical density or the measured changes in current or potential. This invention also relates to a biochemical analysis apparatus for carrying out the method for correcting the results of biochemical analyses. This invention further relates to a correction value recording medium which is used to carry out the method for correcting the results of biochemical analyses and on which a correction value corresponding to the change in characteristics between groups of analysis media is recorded.

2. Description of the Prior Art

Qualitative or quantitative analyses of specific chemical constituents in liquid samples are conducted for various industrial purposes. Particularly, it is very important in biochemical and clinical fields to be able quantitatively to analyze certain chemical or physical constituents in body fluids such as blood or urine.

Recently, dry type chemical analysis slides and test films were developed for use in systems designed for performing quantitative analyses, with which systems the amounts of specific chemical constituents or specific physical constituents contained in droplets of liquid samples, which are applied to the chemical analysis slides or the test films, are determined. For example, film-shaped chemical analysis elements, which are to be used in colorimetry, and chemical analysis slides which accommodate them are disclosed in U.S. Pat. Nos. 3,992,158 and 4,292,272. A film-shaped immunoanalysis (or immunoassay) element, which is to be used in fluorometry or colorimetry, and an immunoanalysis slide which accommodates it are disclosed in European Patent No. 0,051,183A. An immunoanalysis slide which is to be used in fluorometry or colorimetry is disclosed in U.S. Pat. No. 4,587,102. Also, an electrolyte analysis slide comprising a pair of ion selective electrodes, which pair serves as an electrochemical sensor, is disclosed in U.S. Pat. No. 4,053,381. Additionally, electrolyte analysis slides for analyzing a plurality of constituents, each of which slides comprises several pairs of ion selective electrodes serving as electrochemical sensors, are disclosed in U.S. Pat. No. 4,437,970 and European Patent No. 0,212,612A.

It is possible to analyze liquid samples more simply and more quickly with methods in which analysis media such as chemical analysis slides and test films are used than with methods in which conventional wet type analyses are carried out. Therefore, it is more desirable to use chemical analysis slides, particularly in medical organizations, research laboratories, or the like, where many samples must be analyzed, than to carry out conventional wet type analyses.

In order to use an analysis medium, such as a chemical analysis slide or a test film, in the quantitative analysis of a chemical constituent or the like contained in a liquid sample, a droplet of the liquid sample is put on the analysis medium and is kept at a predetermined temperature (i.e. incubated) for a predetermined time in an incubator, which causes a color reaction. The analysis medium is then exposed to light having a wavelength which is selected in advance. The selection of the wavelength depends on the specific biochemical substances contained in the liquid sample and the constituents of a reagent contained in the analysis medium. Light is thus irradiated to the analysis medium, and the optical density is measured. The optical density depends on how much of a reaction product was formed by the reaction between the liquid sample and the reagent in the analysis medium. Thereafter, a calibration curve, which is created in advance and which represents the relationship between the optical densities and the concentrations of the specific biochemical substance in liquid samples, is used in order to determine the concentration of the biochemical substance in the liquid sample from the optical density which was measured.

In order to use a chemical analysis slide comprising at least one pair of ion selective electrodes, which serves as an electrochemical sensor, in the quantitative analysis of a biochemical constituent or the like contained in a liquid sample, a droplet of the liquid sample and a droplet of a reference liquid are respectively put on the ion selective electrodes and are kept at a predetermined temperature (i.e. incubated) for a predetermined time in an incubator, which causes a difference in potential to occur between the ion selective electrodes. The difference in potential is measured. Thereafter, a calibration curve, which is created in advance and which represents the relationship between the differences in potential and the concentrations (or the activities) of a specific biochemical substance in the liquid samples, is used in order to determine the concentration (or the activity) of the biochemical substance in the liquid sample from the measured difference in potential.

A biochemical analysis apparatus has also been proposed with which both the optical density and the current or the difference in potential occurring between at least one pair of ion selective electrodes can be measured.

Problems which occur with a typical example of an analysis conducted with the conventional technique will be described hereinbelow. For this analysis a colorimetric or fluorometric, biochemical analysis method and apparatus are used in order to measure the optical density of the analysis medium, which depends on how much of a reaction product was formed by the reaction between a liquid sample and a reagent in the analysis medium. The same problems also occur with a biochemical analysis method and apparatus wherein an analysis medium provided with an electrochemical sensor is used in order to measure the current or the difference in potential occurring across the electrochemical sensor.

In order to determine the concentration of a specific biochemical substance contained in a liquid sample with a biochemical analysis apparatus, it is necessary to create a calibration curve in advance, which represents the relationship between the optical densities and the concentrations of a specific biochemical substance in liquid samples. The optical densities are measured with an optical densitometer located in the biochemical analysis apparatus. In order to create the calibration curve, the concentrations of the specific biochemical substance in a plurality of liquid samples are measured with one of several methods which have heretofore been established and which are different from the method employed in the biochemical analysis apparatus. Thereafter, the biochemical analysis apparatus is used in order independently to apply the liquid samples to analysis media, such as chemical analysis slides or long test films, and to incubate the analysis media to which the liquid samples have been applied. The optical densities are then measured which depend on how much of a reaction product was formed in the reaction between the liquid samples and the reagent in the analysis media. The optical densities thus measured are plotted on a graph with respect to the corresponding concentrations of the specific biochemical substance in the liquid samples.

FIG. 8 is a graph showing an example of the calibration curve created in the manner described above. In FIG. 8, the optical densities measured with an optical densitometer located in the biochemical analysis apparatus are plotted on the vertical axis, and the concentrations of the specific biochemical substance in liquid samples are plotted on the horizontal axis. The curve indicated by the solid line represents a calibration curve created in the manner described above. Even when the concentration of the specific biochemical substance in a liquid sample is 0.0, the optical density of the analysis medium, such as a chemical analysis slide or a test film, is not equal to 0.0. This is because the background density, i.e. the optical density of the analysis medium with no liquid sample applied thereto, is not equal to 0.0.

However, it often occurs that the optical density, which is measured with an optical densitometer in the manner described above, cannot be directly converted into the concentration of a specific biochemical substance in the liquid sample in accordance with the calibration curve.

The aforesaid calibration curve was created with a biochemical analysis apparatus corrected for accuracy (hereinafter referred to as the "standard biochemical analysis apparatus") and standard analysis media. (A calibration curve created with a standard biochemical analysis apparatus and standard analysis media will hereinafter be referred to as a "standard calibration curve".) A standard calibration curve cannot be directly used to measure the concentration of a specific biochemical substance in a liquid sample. This is primarily because, even when the same liquid sample is applied to a plurality of analysis media, the optical densities of the analysis media will vary in accordance with their characteristics, which should be substantially the same but which differ. The characteristics between production lots of analysis media vary, and a difference in characteristics between groups (for example, packaging units) of analysis media which have been stored for different periods also exists. (Such differences in characteristics will hereinafter be referred to as the "difference in characteristics between a plurality of groups of analysis media".) When the analysis is not required to be highly accurate, the difference in characteristics between a plurality of groups of analysis media can be ignored. When a highly accurate analysis must be conducted, the value of the optical density measured from an analysis medium is corrected, for example, in the manner described below. It is also considered that the biochemical analysis apparatus, which is actually used to carry out analyses, will differ in characteristics from the standard biochemical analysis apparatus. (The biochemical analysis apparatus which is actually used to carry out analyses will hereinafter be referred to as the "object biochemical analysis apparatus".) However, the difference in characteristics between the object biochemical analysis apparatus and the standard biochemical analysis apparatus will not be taken into consideration hereinbelow. This is because, ordinarily, errors in analyses, which are caused by the difference in characteristics between the object biochemical analysis apparatus and the standard biochemical analysis apparatus, are markedly smaller than errors in analyses, which are caused by the difference in characteristics between a plurality of groups of analysis media. Additionally, the difference in characteristics between the object biochemical analysis apparatus and the standard biochemical analysis apparatus can be substantially eliminated if the object biochemical analysis apparatus is appropriately maintained periodically or daily.

In order for the values of the optical densities measured from analysis media to be corrected, three types of standard liquids containing the specific biochemical substance in low (L), middle (M), and high (H) concentrations are prepared. Thereafter, a standard biochemical analysis apparatus is used in order to apply the standard liquids to the standard analysis media. Optical densities are then measured from the standard analysis media. In this manner, as shown in FIG. 8, optical densities DL, DM, and DH are measured for the three types of standard liquids. Therefore, from the calibration curve (i.e. the standard calibration curve) indicated by the solid line in FIG. 8, the concentrations of the specific biochemical substance in the three types of standard liquids are measured as being CL, CM, and CH. It is only necessary for the standard liquids to be prepared so that they always contain their constituents in a stable state. The concentrations CL, CM, and CH measured in the manner described above need not necessarily be equal to the correct concentrations of the specific biochemical substance in the three types of standard liquids. Thereafter, the object biochemical analysis apparatus is used in order to apply the standard liquids to analysis media, which are actually to be used in order to analyze liquid samples, and to measure the optical densities from the analysis media. (The analysis media which are actually to be used in order to analyze liquid samples will hereinafter be referred to as the "object analysis media". Also, because the difference in characteristics between the object biochemical analysis apparatus and the standard biochemical analysis apparatus is ignored, the standard biochemical analysis apparatus may be used at this time.) In cases where optical densities DL', DM', and DH' are thus measured from the object analysis media, the standard calibration curve is corrected into the calibration curve indicated by the broken line in FIG. 8, with which calibration curve the optical densities DL', DM', and DH' are respectively converted into the concentrations CL, CM, and CH. (The calibration curve which has thus been corrected will hereinafter be referred to as the "corrected calibration curve".)

After the corrected calibration curve is created in the manner described above, information about the corrected calibration curve is recorded in association with the corresponding object analysis media. For example, the method described below is employed, which is equivalent to the creation of a corrected calibration curve. Specifically, the standard calibration curve is used in order to measure concentrations CL', CM', CH' of the specific biochemical substance, which correspond respectively to the optical densities DL', DM', and DH' measured from the object analysis media. Thereafter, the concentrations CL', CM', CH' are respectively substituted into the quadratic equation $$C = c(C')^2 + d(C') + e \qquad (1)$$

wherein C' represents the concentration of the specific biochemical substance, the variation in which concentration has not been corrected for, and C represents the concentration of the specific biochemical substance, the variation in which concentration has been corrected for. In this manner, the coefficients c, d, and e are calculated. Information about the three coefficients is, for example, written on a sheet of paper, and the sheet of paper is packaged together with the object analysis media. Information about the standard calibration curve is stored in advance in the object biochemical analysis apparatus, in which object analysis media are used in order to measure concentrations of the specific biochemical substance in liquid samples. Before object analysis media are used in the object biochemical analysis apparatus, the information about the coefficients c, d, and e is entered into the object biochemical analysis apparatus. Thereafter, the object biochemical analysis apparatus applies a droplet of a liquid sample to an object analysis medium, and the concentration C' of the specific biochemical substance is measured, the variation in which concentration has not been corrected for. Equation (1) is then used in order to calculate the corrected value of the concentration C of the specific biochemical substance from the measured concentration C'. In this manner, the liquid sample can be analyzed accurately.

The technique for correcting the standard calibration curve in the manner described above is disclosed in, for example, European Patent No. 0,247,439A. This reference teaches that, when different calibration curves are required for different batches of test media (i.e. when the characteristics of the test media differ between groups of the test media), information about how the calibration curve should be corrected is indicated with a bar code for each package (or each container) of the same batch of test media. The bar code is recorded on the packaging material or on a film separate from the test media. However, with the disclosed technique, the calibration curve is corrected manually. Specifically, information which instructs how the calibration curve is to be corrected is manually entered from a keyboard of the analysis apparatus in accordance with the information recorded on the packaging material or the film.

In cases where the difference in characteristics between a plurality of groups of analysis media is small (but is so large that the calibration curve must be corrected), the method described below is employed. The method will hereinbelow be described with reference to FIG. 9: FIG. 9 is an explanatory graph showing a different method for correcting a calibration curve.

In FIG. 9, the horizontal axis of the graph represents concentrations C1 of the specific biochemical substance, which were measured with a conventional analysis system other than the biochemical analysis apparatus. The vertical axis represents concentrations C2 of the specific biochemical substance, which were measured with the biochemical analysis apparatus. The solid line represents the relationship between the concentrations C1 and the concentrations C2, which concentrations C2 were measured with the standard biochemical analysis apparatus and the standard analysis media. In cases where the standard calibration curve was created accurately, C2=C1, i.e. the solid line takes on the form of a straight line which passes through the origin of the graph and has a slope equal to 1.0. The broken line represents the relationship between the concentrations C1 and the concentrations C2, which concentrations C2 were measured with the object biochemical analysis apparatus and the object analysis media. (Because the difference in characteristics between the object biochemical analysis apparatus and the standard biochemical analysis apparatus is ignored, the standard biochemical analysis apparatus may be used in lieu of the object biochemical analysis apparatus.) Because the difference in characteristics is present between a plurality of groups of analysis media, the broken line takes on the form of a straight line expressed as $$C2 = p \cdot C1 + q \qquad (2)$$

In cases where the difference in characteristics between a plurality of groups of analysis media is small, instead of the information about the coefficients c, d, and e being recorded, information about the coefficients p and q is recorded in association with the corresponding object analysis media. When the object analysis media are used in the object biochemical analysis apparatus in order to analyze liquid samples, values obtained from the analyses are corrected with the coefficients p and q. In this manner, the liquid samples can be analyzed accurately.

Heretofore, an operator of the object biochemical analysis apparatus has had manually to input the information about the coefficients c, d, and e or the information about the coefficients p and q from a keyboard, or the like, into the object biochemical analysis apparatus. Therefore, a problem often occurs because incorrect information is entered by mistake into the object biochemical analysis apparatus, and incorrect results of analyses are obtained from the object biochemical analysis apparatus. Even when this problem occurs, it is not easy to recognize that the problem has occurred. Additionally, the manual input of the information is troublesome.

The method described below has been suggested for eliminating these problems. For example, a bar code, which represents the information about the coefficients c, d, and e or the information about the coefficients p and q, is recorded on each object analysis medium. Also, a bar code reader is located in the object biochemical analysis apparatus. After the analysis medium is put into the object biochemical analysis apparatus, the bar code is automatically read from the analysis medium by the bar code reader and entered into the object biochemical analysis apparatus.

In general, so that the analysis media can be produced efficiently, a sheet or a tape having a large area, from which a large number of analysis media are to be produced, is prepared and stored. When the analysis media are produced from the sheet or the tape, the sheet or the tape is slit and cut into a plurality of pieces. The pieces are then inserted into slide mounts (or slide frames) and subjected to processes such as aging. In this manner, the analysis media are completed. The single sheet or the single tape, from which a large number of analysis media are produced, constitutes a single production lot. If the production lot exhibited approximately uniform characteristics during the production process and little change in characteristics during storage, and if the processes, such as the aging, of the pieces cut from the sheet or the tape were carried out under exactly the same conditions, it would be possible to employ the method described below. Specifically, in order to allow the coefficients c, d, and e or the coefficients p and q to be determined, a small number of pieces are slit and cut from the sheet or the tape. The pieces are then inserted into mounts and subjected to processes such as aging. A small number of analysis media thus produced are then used in order to determine the coefficients c, d, and e or the coefficients p and q. Thereafter, the information about the coefficients c, d, and e or the information about the coefficients p and q is recorded on many mounts. The remaining part of the sheet or the tape is then slit and cut into pieces. The pieces thus obtained are inserted into the mounts, on which the information about the coefficients c, d, and e or the information about the coefficients p and q has been recorded. The pieces which have been inserted into the mounts are then subjected to processes such as aging. In this manner, it would be possible to produce the analysis media on which the information about the coefficients c, d, and e or the information about the coefficients p and q has been recorded.

However, actually, some types of analysis media have a high sensitivity, and their characteristics easily change due to ambient temperature and humidity, and due to solvents, or the like, which are contained in the ambient air. For analysis media having a high sensitivity, the problem described below occurs. Specifically, the coefficients c, d, and e or the coefficients p and q are determined for analysis media having a high sensitivity in the manner described above, and the information about the coefficients is recorded on the mounts. Thereafter, the pieces cut from the sheet or the tape, from which such analysis media are produced, are inserted into the mounts, and subjected to processes such as aging. In the course of such analysis media being produced, the characteristics thereof become different from the characteristics of the analysis media, which were used in order to determine the coefficients c, d, and e or the coefficients p and q. Such a difference in characteristics is caused by, for example, a small difference in the conditions, under which the sheet or the tape was stored, and particularly by a small difference in the conditions under which the pieces inserted into the mounts were aged. Also, a high cost and considerable labor are required to prepare in advance the mounts on which the information about the coefficients c, d, and e or the information about the coefficients p and q has been recorded.

In order to solve these problems, the method described below has been suggested. Specifically, mounts on which no information about the coefficients has been recorded are prepared. Pieces cut from the sheet or the tape are then inserted into the mounts and subjected to processes such as aging. Thereafter, the coefficients c, d, and e or the coefficients p and q are determined from the analysis media thus produced, and the information about the coefficients are printed on the mounts of the analysis media.

However, analysis media having a high sensitivity are easily affected by a solvent contained in the printing ink, and the solvent causes the characteristics of the analysis media to change.

A method wherein the information about the coefficients c, d, and e or the information about the coefficients p and q is printed on labels and the labels are adhered to the mounts of the analysis media might also be considered. However, with this method, there is the risk of the analysis media being adversely affected by the adhesive which is used to adhere the labels to the mounts.

As described above, information about the coefficients c, d, and e or information about the coefficients p and q is necessary in order to correct the results of biochemical analyses. Additionally, other information, such as the name of the biochemical substance which is to be analyzed with the analysis media, is necessary in order to specify the analysis media. On the other hand, the mounts of the analysis media are used primarily for the purpose of supporting the analysis media. When a bar code, or the like, is recorded on a mount, the area over which the bar code, or the like, can be recorded is limited, and the bar code, or the like, must be recorded accurately. Therefore, a limitation is imposed on the amount of the information (for example, the number of code digits representing the information) which can be recorded on the mount. For this reason, a problem occurs in that there is not enough space to record the information necessary for correcting the results of the biochemical analyses (such as the information about the coefficients c, d, and e or the information about the coefficients p and q). For example, when the information about the coefficients c, d, and e is to be recorded in order to cope with large differences in characteristics between production lots of the analysis media, it is necessary for the code to have 12 digits (i.e. 4 digits $\times$ 3). Even when the differences between production lots of the analysis media are small and information about the coefficients p and q is to be recorded, it is necessary for the code to have, for example, 4 digits (i.e. 2 digits $\times$ 2). It is difficult to record such a large amount of information on a mount, or the like, together with the other necessary information, such as the name of the biochemical substance.

SUMMARY OF THE INVENTION

The primary object of the present invention is to provide a method for correcting the results of biochemical analyses wherein problems accompanying the printing, or the like, of information on slide mounts (or slide frames) of analysis media, or the like, are eliminated.

Another object of the present invention is to provide a method for correcting the results of biochemical analyses wherein, even when analysis media having a high sensitivity are used, correction values to be used in order to correct the results of biochemical analyses are recorded so that it is clear which correction values correspond to which analysis media.

A further object of the present invention is to provide a biochemical analysis apparatus for carrying out the method for correcting the results of biochemical analyses.

A still further object of the present invention is to provide a correction value recording medium on which the information about correction values to be used in order to correct the results of biochemical analyses is recorded.

The specific object of the present invention is to eliminate the problems occurring when information about correction values to be used in order to correct the results of biochemical analyses is manually entered from a keyboard, or the like, into a biochemical analysis apparatus, which often results in incorrect information being entered by mistake, and to eliminate the manual operation for entering the information about correction values, which operation is troublesome.

The present invention provides a first biochemical analysis apparatus wherein droplets of liquid samples are independently applied (by spotting or putting) to analysis media containing a reagent or an electrochemical sensor, which will interact with a specific biochemical substance (an analyte) contained in the liquid samples and give rise to changes in the analysis media, the changes which have occurred in the analysis media are measured, and thereafter a calibration curve, which represents the relationship between values thus measured and concentrations or activities of the specific biochemical substance in the liquid samples, is used in order to determine the concentrations or the activities of the specific biochemical substance from the values thus measured, wherein the improvement comprises the provision of:

i) a movement means which moves analysis media along a movement path connecting an introducing section, from which analysis media are introduced into said biochemical analysis apparatus, and an ejecting section into which analysis media, after they have been used in analyses, are ejected from said biochemical analysis apparatus, ii) a measurement means for measuring changes, which have occurred in analysis media, while the analysis media are present in said movement path, iii) a storage means which stores information about said calibration curve, iv) a reading means for reading information about correction values, which are to be used in order to correct said calibration curve into a calibration curve suitable for analysis media used in the analyses, from a correction value recording medium on which said information about said correction values has been recorded, v) a correction means for correcting said calibration curve, which is represented by the information read from said storage means, on the basis of said correction values which are represented by the information read from said correction value recording medium, and vi) an operation means which uses the corrected calibration curve in order to determine the concentration or the activity of the specific biochemical substance in a liquid sample from the value measured by said measurement means.

The present invention also provides a second biochemical analysis apparatus wherein the first biochemical analysis apparatus in accordance with the present invention is modified in such a way that said reading means reads information about correction values from a correction value recording medium, which is shaped so that it is capable of being moved along said movement path in lieu of an analysis medium, while said correction value recording medium is present in said movement path.

The present invention further provides a third biochemical analysis apparatus wherein the first or second biochemical analysis apparatus in accordance with the present invention is modified in such a way that said reading means reads information about correction values from a correction value recording medium and reads information, which gives specifics about analysis media corresponding to a correction value recording medium and which is recorded on the correction value recording medium together with the information about correction values, a second reading means is provided which reads information from the analysis media while they are present in said movement path, said information giving specifics about a correction value recording medium corresponding to analysis media and being recorded on the analysis media, and a judgment means is provided which judges whether the information, which gives specifics about analysis media corresponding to a correction value recording medium and which has been read with said first reading means, and the information, which gives specifics about a correction value recording medium corresponding to analysis media and which has been read with said second reading means, correspond or do not correspond to each other.

The present invention still further provides a fourth biochemical analysis apparatus wherein the third biochemical analysis apparatus in accordance with the present invention is modified in such a way that said first reading means reads information about correction values and information, which gives specifics about analysis media corresponding to a correction value recording medium, from a correction value recording medium, which is shaped so that it is capable of being moved along said movement path in lieu of an analysis medium, while said correction value recording medium is present in said movement path.

The present invention also provides a fifth biochemical analysis apparatus wherein the fourth biochemical analysis apparatus in accordance with the present invention is modified in such a way that said first reading means also serves as said second reading means and reads information, which gives specifics about a correction value recording medium corresponding to analysis media and which is recorded on the analysis media, from the analysis media while they are present in said movement path.

The present invention further provides a first method for correcting the results of biochemical analyses wherein a variation in values obtained from biochemical analyses, which is caused by a difference in characteristics between a plurality of groups of analysis media, is eliminated in biochemical analyses in which droplets of liquid samples are independently applied to analysis media containing a reagent or an electrochemical sensor, which will interact with a specific biochemical substance contained in the liquid samples and give rise to changes in the analysis media, the changes which have occurred in the analysis media are measured, and thereafter a calibration curve, which represents the relationship between the values thus measured and the concentrations or activities of the specific biochemical substance in the liquid samples, is used in order to determine the concentrations or the activities of the specific biochemical substance from the values thus measured, the method for correcting the results of biochemical analyses comprising the steps of:

i) creating a predetermined calibration curve which is used in the course of determining the concentrations or the activities of the specific biochemical substance in the liquid samples from biochemical analyses which are carried out with analysis media having predetermined characteristics, ii) determining correction values for correcting said predetermined calibration curve in order to determine the concentrations or the activities of the specific biochemical substance in the liquid samples from biochemical analyses which are carried out with analysis media having different characteristics from said analysis media having predetermined characteristics, iii) recording the information about said correction values on a correction value recording medium which is independent of the analysis media, iv) storing the information about said predetermined calibration curve in the storage means of the first or second biochemical analysis apparatus in accordance with the present invention, and v) in the course of using the biochemical analysis apparatus in order to determine the concentrations or the activities of the specific biochemical substance in the liquid samples, causing the reading means of the biochemical analysis apparatus to read the information about said correction values from said correction value recording medium.

The present invention still further provides a second method for correcting the results of biochemical analyses wherein a variation in values obtained from biochemical analyses, which is caused by a difference in characteristics between a plurality of groups of analysis media, is eliminated in biochemical analyses in which droplets of liquid samples are independently applied to analysis media containing a reagent or an electrochemical sensor, which will interact with a specific biochemical substance contained in the liquid samples and give rise to changes in the analysis media, the changes which have occurred in the analysis media are measured, and thereafter a calibration curve, which represents the relationship between values thus measured and concentrations or activities of the specific biochemical substance in the liquid samples, is used in order to determine the concentrations or the activities of the specific biochemical substance from the values thus measured, the method for correcting the results of biochemical analyses comprising the steps of:

i) creating a predetermined calibration curve which is used in the course of determining the concentrations or the activities of the specific biochemical substance in the liquid samples from biochemical analyses which are carried out with analysis media having predetermined characteristics, ii) determining correction values for correcting said predetermined calibration curve in order to determine the concentrations or the activities of the specific biochemical substance in the liquid samples from biochemical analyses which are carried out with analysis media having different characteristics from said analysis media having predetermined characteristics, iii) recording the information about said correction values on a correction value recording medium which is independent of the analysis media, iv) recording the information, which gives specifics about a correction value recording medium corresponding to analysis media, on the analysis media, and recording the information, which gives specifics about analysis media corresponding to a correction value recording medium, on the correction value recording medium, v) storing the information about said predetermined calibration curve in the storage means of the third, fourth, or fifth biochemical analysis apparatus in accordance with the present invention, vi) causing the reading means of the biochemical analysis apparatus to read the information about said correction values and the information, which gives specifics about analysis media corresponding to a correction value recording medium, from said correction value recording medium, and vii) thereafter using the biochemical analysis apparatus in order to determine the concentrations or the activities of the specific biochemical substance in the liquid samples.

The present invention also provides a correction value recording medium for use in the second, fourth, or fifth biochemical analysis apparatus in accordance with the present invention, the correction value recording medium being shaped so that it is capable of being moved along said movement path in the biochemical analysis apparatus in lieu of an analysis medium.

The term "group of analysis media" as used herein means a group of analysis media which can be regarded as having the same performance with respect to the required accuracy of analyses or the like. By way of example, the term "group of analysis media" as used herein means a production lot of analysis media.

The term "correction means for correcting a calibration curve which is represented by the information read from a storage means" as used herein means a correction means which substantially corrects a calibration curve. Also, the term "operation means which uses a corrected calibration curve in order to determine the concentration or the activity of a specific biochemical substance in a liquid sample from the value measured by a measurement means" as used herein means an operation means which carries out an operation in order to determine the correct concentration or activity of a specific biochemical substance in a liquid sample on the basis of a calibration curve which has been substantially corrected. For example, the calibration curve need not necessarily be corrected by itself, and the correction means and the operation means may be constituted so that a concentration $C'$ of a specific biochemical substance measured from the calibration curve is converted into a correct concentration $C$ in accordance with Equation (1).

In major embodiments of the first to fifth biochemical analysis apparatuses in accordance with the present invention, the reading means is located facing the movement path, along which the analysis media are moved, as in the second, fourth, and fifth biochemical analysis apparatuses in accordance with the present invention. However, in the first and third biochemical analysis apparatuses in accordance with the present invention, the reading means need not necessarily be associated with the movement path, but may be located on the side outward from the biochemical analysis apparatus. In such cases, the correction value recording medium need not necessarily be shaped so that it is capable of being moved along the movement path in lieu of an analysis medium. As disclosed in European Patent No. 0,247,439A, correction values may be recorded on an outer surface of a package or a container of analysis media.

How a calibration curve is corrected will hereinbelow be described for cases wherein the concentration of a biochemical substance in a liquid sample is determined. In cases where the activity of a biochemical substance in a liquid sample is to be determined, a calibration curve can be corrected in the same manner as the calibration curve for the concentration. The activity is determined mainly when the biochemical substance which is to be analyzed is an enzyme. However, the term "activity" as used herein also embraces the activity which, is determined when the constituent which is to be analyzed is an electrolyte (which is ionized into, for example, $Na^+$ ions, $K^+$ ions, $Cl^-$ ions, or carbonate ions). Also, the term "analysis media" as used herein embraces analysis media which are provided with hydrophilic polymer binder layers and which contain no reagent in the narrow sense. One example of such analysis media is a sheet-like, integral type, multi-layer analysis element, as disclosed in U.S. Pat. No. 4,337,222. The multi-layer analysis element is used to determine concentrations of hemoglobin and comprises a transparent support material, a gelatin layer and a fabric spreading layer, which layers are overlaid in this order on the transparent support material. The biochemical analysis apparatuses, the methods for correcting the results of biochemical analyses, and the correction value recording medium in accordance with the present invention are applicable also when the concentration or the activity of a chemical substance other than biochemical substances is determined. Therefore, the term "biochemical substance" as used herein should be interpreted in a broad sense and embraces a chemical substance.

With the first method for correcting the results of biochemical analyses in accordance with the present invention, the predetermined calibration curve is created, and correction values for correcting the predetermined calibration curve are determined. The information about the correction values is recorded with a bar code, or the like, on a correction value recording medium which is independent of the analysis media, such as a card packaged together with the analysis media, or a box used to package the analysis media. Therefore, it is possible to eliminate the problems which occur when the information about the correction values is printed in advance on a mount, or the like, which constitutes an analysis medium. It is also possible to eliminate the problems which occur when the information about the correction values is printed on an analysis medium or the mount thereof after the analysis medium has been completed (for example, after the analysis medium has been inserted into the amount), or when a label, on which the information about the correction values has been printed, is adhered to the analysis medium or the mount thereof after the analysis medium has been completed.

In the first method for correcting the results of biochemical analyses, the concentration of the specific biochemical substance is determined with the first or second biochemical analysis apparatus in accordance with the present invention. In the course of the concentration of the specific biochemical substance being determined with the biochemical analysis apparatus, the information about the correction values is read with the reading means of the biochemical analysis apparatus from the correction value recording medium. Therefore, it is possible to eliminate the problems occurring because the information about correction values is manually entered from a keyboard, or the like, into a biochemical analysis apparatus, which often results in incorrect information being entered by mistake. It is also possible to eliminate the manual operation for entering the information about correction values, which operation is troublesome.

No limitation is imposed on whether the information about the correction values is read from the correction value recording medium before or after the optical density is measured from the analysis medium to which a liquid sample has been applied. It is only necessary for the information about the correction values to be read before the concentration of the specific biochemical substance is ultimately determined.

With the first biochemical analysis apparatus in accordance with the present invention, the measurement means measures the optical density from the analysis medium to which a liquid sample has been applied. The storage means stores the predetermined calibration curve. The reading means reads the information about the correction values from the correction value recording medium, and the correction means corrects the predetermined calibration curve. Also, the operation means uses the corrected calibration curve in order to determine the concentration of the specific biochemical substance in the liquid sample from the optical density measured with the measurement means. Therefore, with the first biochemical analysis apparatus in accordance with the present invention, the first method for correcting the results of biochemical analyses in accordance with the present invention can be carried out in order accurately to analyze liquid samples. Also, because the first biochemical analysis apparatus in accordance with the present invention is provided with the reading means, it can eliminate the problems which accompany the manual operation for entering the information about correction values.

With the second biochemical analysis apparatus in accordance with the present invention, the first biochemical analysis apparatus in accordance with the present invention is modified so that the correction value recording medium in accordance with the present invention is used, and the reading means reads the information about the correction values from the correction value recording medium while the correction value recording medium is present in the movement path. Therefore, with the second biochemical analysis apparatus in accordance with the present invention, the same effects as with the first biochemical analysis apparatus in accordance with the present invention are obtained. Additionally, the second biochemical analysis apparatus in accordance with the present invention can be operated easily without a particular manual operation being required to correct the results of biochemical analyses.

With the second method for correcting the results of biochemical analyses in accordance with the present invention, the first method for correcting the results of biochemical analyses in accordance with the present invention is modified so that the information, which gives specifics about a correction value recording medium corresponding to analysis media, is recorded on the analysis media, and the information, which gives specifics about analysis media corresponding to a correction value recording medium, is recorded on the correction value recording medium. The reading means of the third, fourth, or fifth biochemical analysis apparatus in accordance with the present invention reads the information about the correction values and the information, which gives specifics about analysis media corresponding to a correction value recording medium, from the correction value recording medium. Concentrations of the specific biochemical substance in liquid samples are then determined with the third, fourth, or fifth biochemical analysis apparatus in accordance with the present invention. The third, fourth, and fifth biochemical analysis apparatuses in accordance with the present invention are provided with the second reading means, which reads information from the analysis media while they are present in the movement path, said information giving specifics about a correction value recording medium corresponding to analysis media and being recorded on the analysis media. The biochemical analysis apparatus is also provided with the judgment means, which judges whether the correction value recording medium, from which the information about the correction values has been read with the first reading means, and the analysis media, from which the information giving specifics about a correction value recording medium corresponding to analysis media has been read with the second reading means, correspond or do not correspond to each other. Therefore, with the second method for correcting the results of biochemical analyses in accordance with the present invention, the same effects as with the first method for correcting the results of biochemical analyses in accordance with the present invention are obtained. Also, when the information about correction values is read from a correction value recording medium, which does not correspond to the analysis media being used in biochemical analyses, a warning can be issued or the operation of the biochemical analysis apparatus can be stopped in order to prevent incorrect results from being obtained from the biochemical analyses, and to prevent the problems accompanying incorrect biochemical analyses from occurring.

The third biochemical analysis apparatus in accordance with the present invention carries out the second method for correcting the results of biochemical analyses in accordance with the present invention. Therefore, with the third biochemical analysis apparatus in accordance with the present invention, the same effects as with the first biochemical analysis apparatus in accordance with the present invention can be obtained. Additionally, biochemical analyses can be prevented from being carried out with a correction value recording medium and analysis media which do not correspond to each other. Therefore, it is possible to prevent incorrect results from being obtained from the biochemical analyses, and to prevent the analysis media from being used uselessly.

With the fourth biochemical analysis apparatus in accordance with the present invention, the third biochemical analysis apparatus in accordance with the present invention is modified so that the correction value recording medium in accordance with the present invention is used, and the first reading means reads the information about the correction values and information, which gives specifics about analysis media corresponding to a correction value recording medium, from the correction value recording medium while the correction value recording medium is present in the movement path. Therefore, with the fourth biochemical analysis apparatus in accordance with the present invention, the same effects as with the third biochemical analysis apparatus in accordance with the present invention are obtained. Additionally, the fourth biochemical analysis apparatus in accordance with the present invention can be operated easily without a particular manual operation being required to correct the results of biochemical analyses.

With the fifth biochemical analysis apparatus in accordance with the present invention, the fourth biochemical analysis apparatus in accordance with the present invention is modified in such a way that the first reading means also serves as the second reading means. Therefore, with the fifth biochemical analysis apparatus in accordance with the present invention, the same effects as with the fourth biochemical analysis apparatus in accordance with the present invention can be obtained. Additionally, the cost of the biochemical analysis apparatus can be kept low, and the biochemical analysis apparatus can be kept small in size.

The correction value recording medium in accordance with the present invention is shaped so that it is capable of being moved along the movement path of the analysis media in the biochemical analysis apparatus in lieu of an analysis medium. By way of example, the correction value recording medium may have approximately the same shape as an analysis medium. Therefore, accurate biochemical analyses can be carried out easily when the correction value recording medium is used in the second, fourth, or fifth biochemical analysis apparatus in accordance with the present invention. Also, the correction value recording medium is separate from the analysis media. Accordingly, the material of the correction value recording medium can be selected from those which enable clear and accurate printing, and a large amount of information can be recorded on the correction value recording medium.

DESCRIPTION OF THE PREFERRED EMBODIMENTS

The present invention will hereinbelow be described in further detail with reference to the accompanying drawings.

Figure 1:
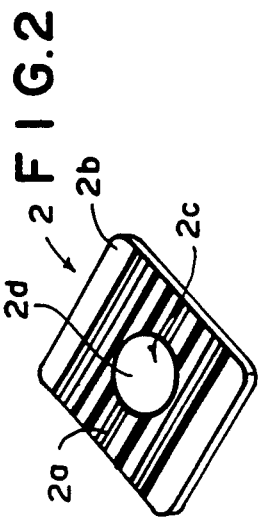
FIG. 1 is a perspective view showing a correction slide which is an embodiment of the correction value recording medium in accordance with the present invention.
Figure 8:
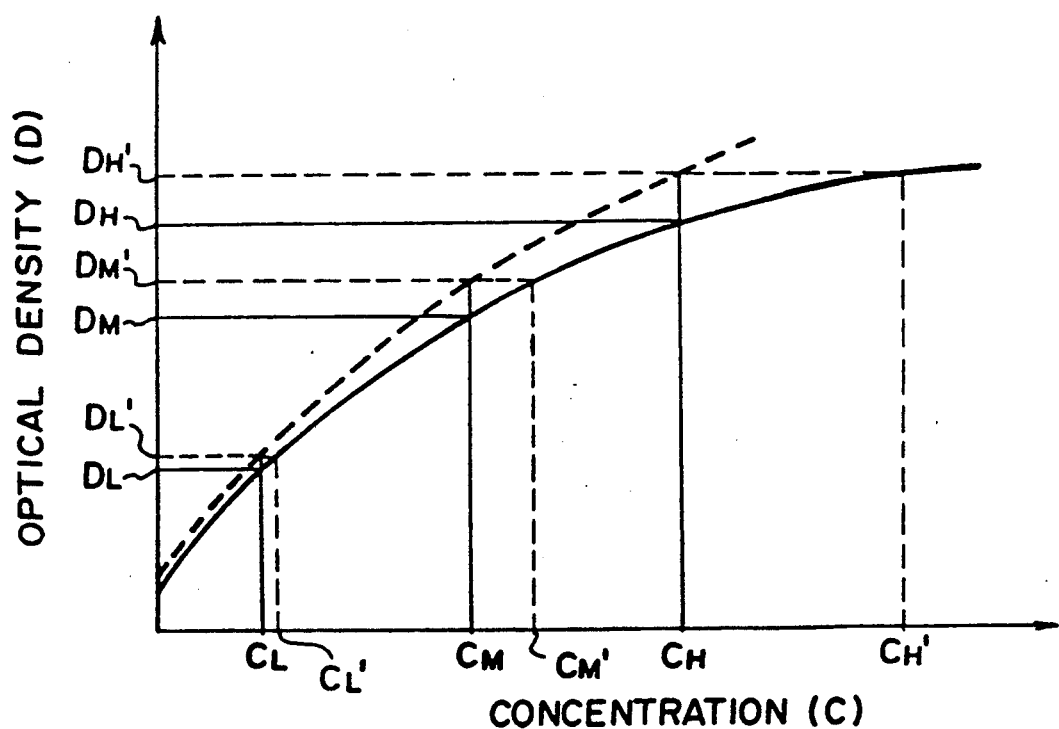
FIG. 8 is an explanatory graph showing how a calibration curve is corrected.
Figure 9:
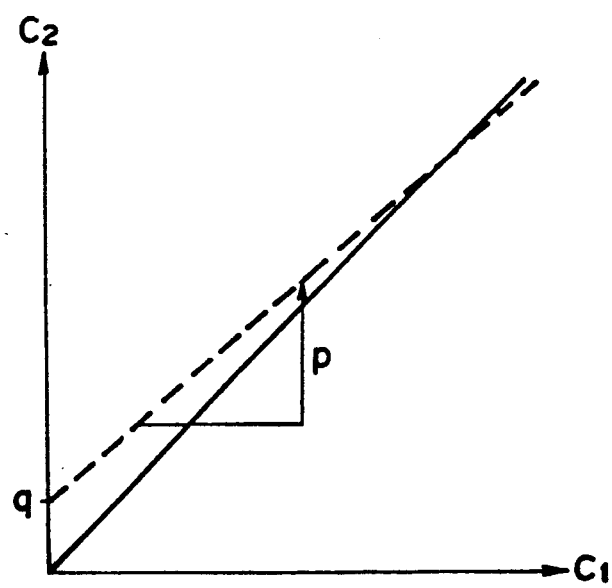
FIG. 9 is an explanatory graph showing another method for correcting a calibration curve.

FIG. 1 shows a correction slide 1 which is an embodiment of the correction value recording medium in accordance with the present invention. The correction slide 1 has the same outer dimensions as a chemical analysis slide 2 shown in FIG. 2, and a bar code 1a is printed on the correction slide 1. The correction slide 1 is constituted of a material suitable for having a bar code 1a printed thereon. Therefore, even thin lines can be printed clearly and precisely. By way of example, six digits of a code are printed on the correction slide 1. The bar code 1a comprising six digits represents correction values, which are used to correct the standard calibration curve indicated by the solid line in FIG. 8 into a calibration curve suitable for a group of chemical analysis slides 2, 2, . . . Also, in this embodiment, the bar code 1a represents the lot number of the chemical analysis slides 2, 2, . . . corresponding to the correction slide 1. By way of example, information about the coefficients p and q described above is printed on the correction slide 1 and represents information about the correction values. The coefficients p and q are determined in the manner described above. The manufacturer who produces the chemical analysis slides 2, 2, . . . determines the correction values, prints the information about the correction values on the correction slide 1, and supplies the correction slide 1 with the chemical analysis slides 2, 2, . . . to a user.

Figure 2:
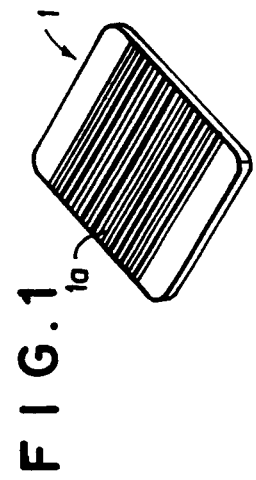
FIG. 2 is a perspective view showing a chemical analysis slide which is an example of an analysis medium.

FIG. 2 shows the chemical analysis slide 2 which is an example of an analysis medium.

With reference to FIG. 2, the chemical analysis slide 2 comprises a mount 2b having an opening 2c, through which a droplet of a liquid sample, such as blood or urine, is to be applied, and a film-shaped chemical analysis element 2d which is inserted in the specific biochemical substance contained in a liquid sample. (The film-shaped chemical analysis element 2d will hereinafter be often referred to as the film 2d.) A bar code 2a is printed on the mount 2b of the chemical analysis slide 2. The bar code 2a comprises four digits which represent the name of the biochemical substance to be analyzed with the chemical analysis slide 2, and the lot number of the chemical analysis slide 2. The primary purpose of the mount 2b is to support the film 2d, and very thin lines cannot be printed on the mount 2b. Therefore, only four digits of code are recorded on the mount 2b. The film 2d is very sensitive, and ambient conditions, such as the ambient temperature and humidity, and the constituents contained in ambient air can easily cause it to change its characteristics. Therefore, the film 2d is processed carefully.

Also, for the reasons described above, in the course of producing the chemical analysis slide 2, the bar code 2a is printed on the mount 2b before the film 2d is inserted into the mount 2b. After the ink printed on the mount 2b has dried and there is no risk of the solvent, or the like, contained in the ink adversely affecting the film 2d, the film 2d is inserted into the mount 2b and subjected to processes such as aging. In this manner, the chemical analysis slide 2 is completed.

Figure 3:
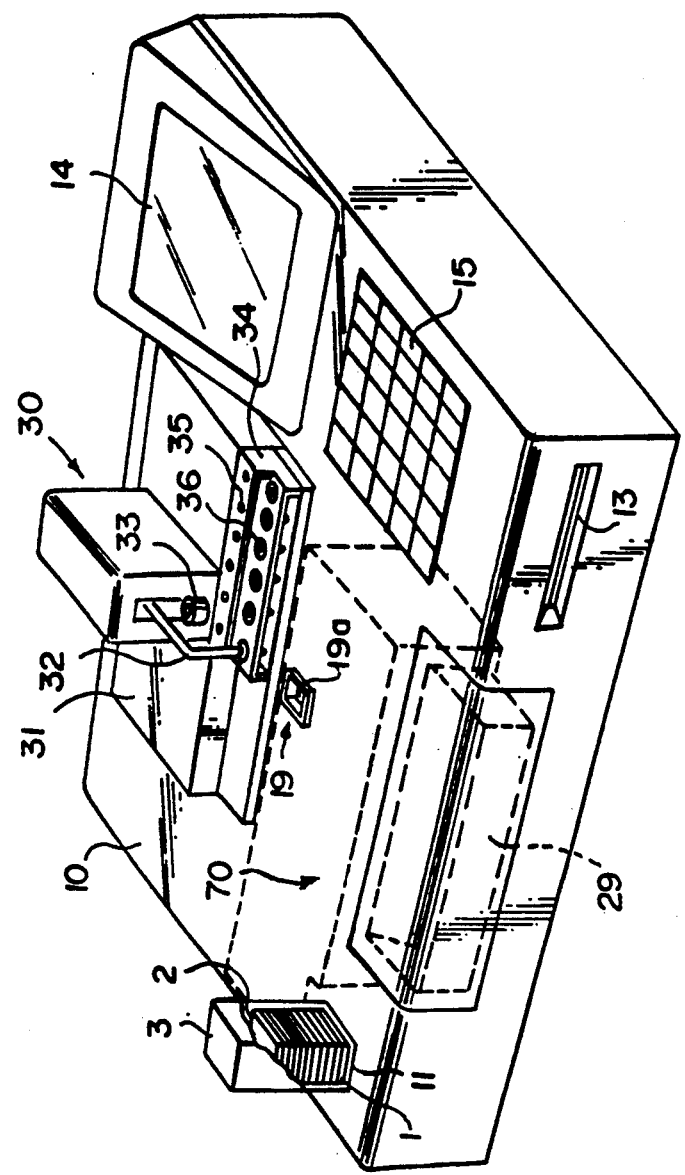
FIG. 3 is a perspective view showing an embodiment of the biochemical analysis apparatus in accordance with the present invention.
Figure 4:
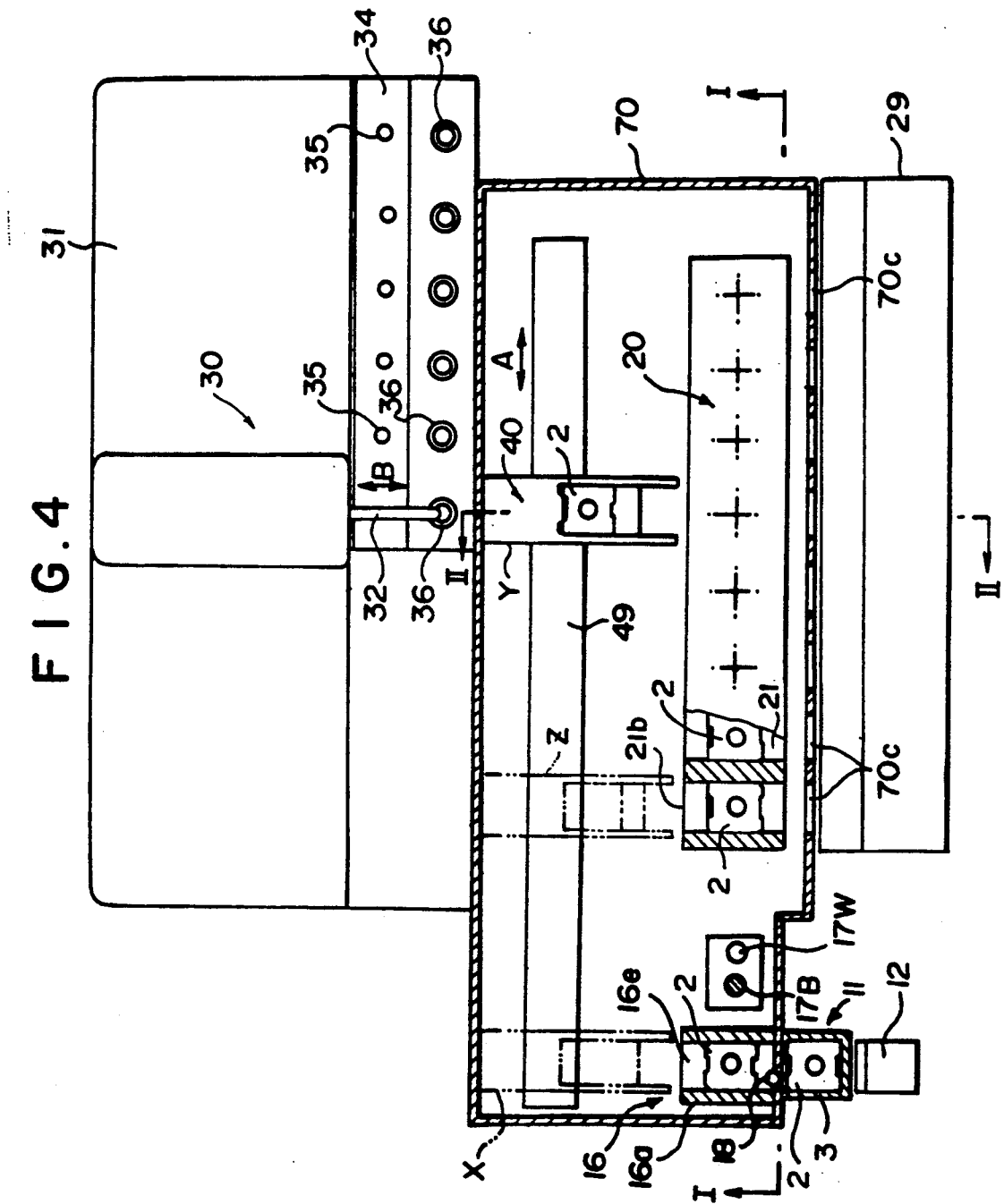
FIG. 4 is a plan view showing the major part of the biochemical analysis apparatus shown in FIG. 3, with a housing thereof being omitted.
Figure 5:
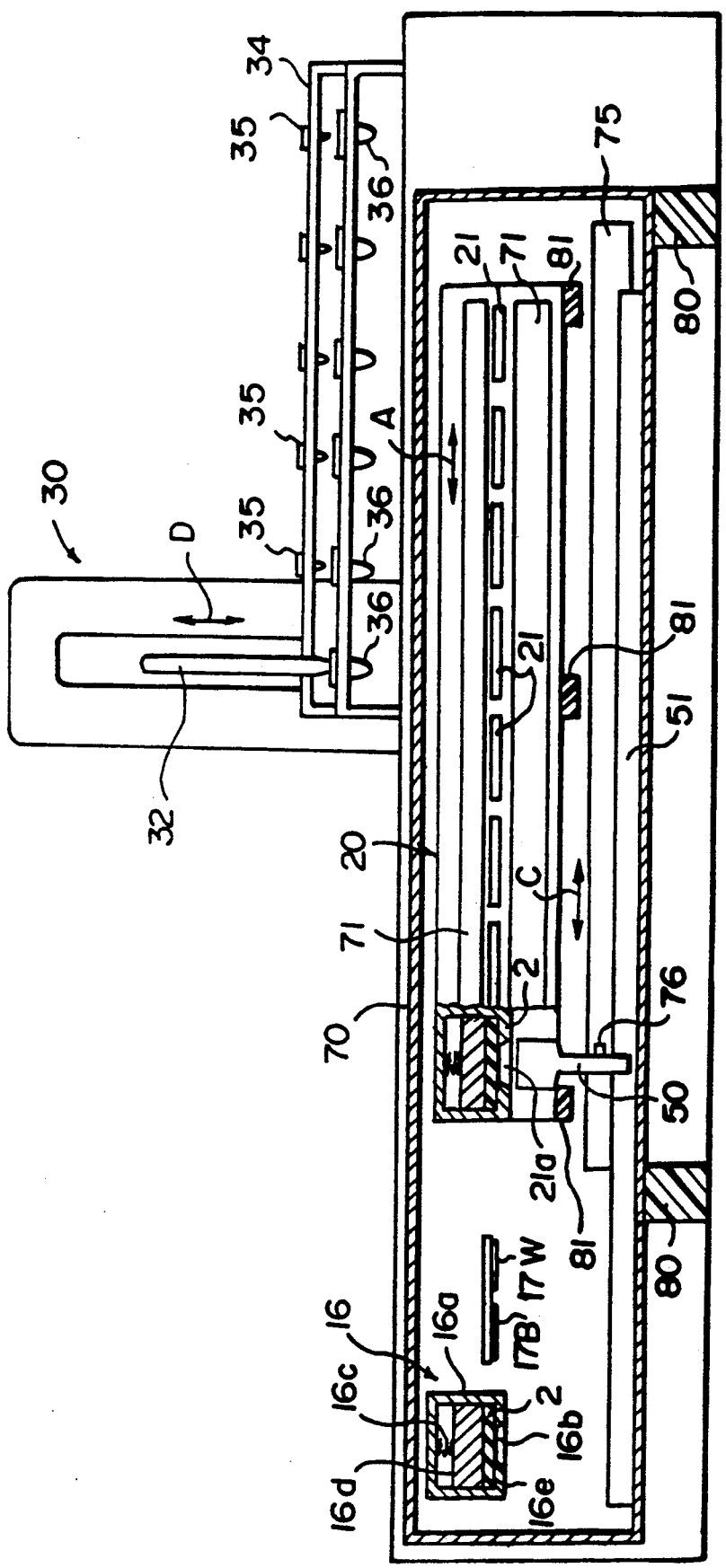
FIG. 5 is a sectional front view taken along line I—I of FIG. 4.
Figure 6:
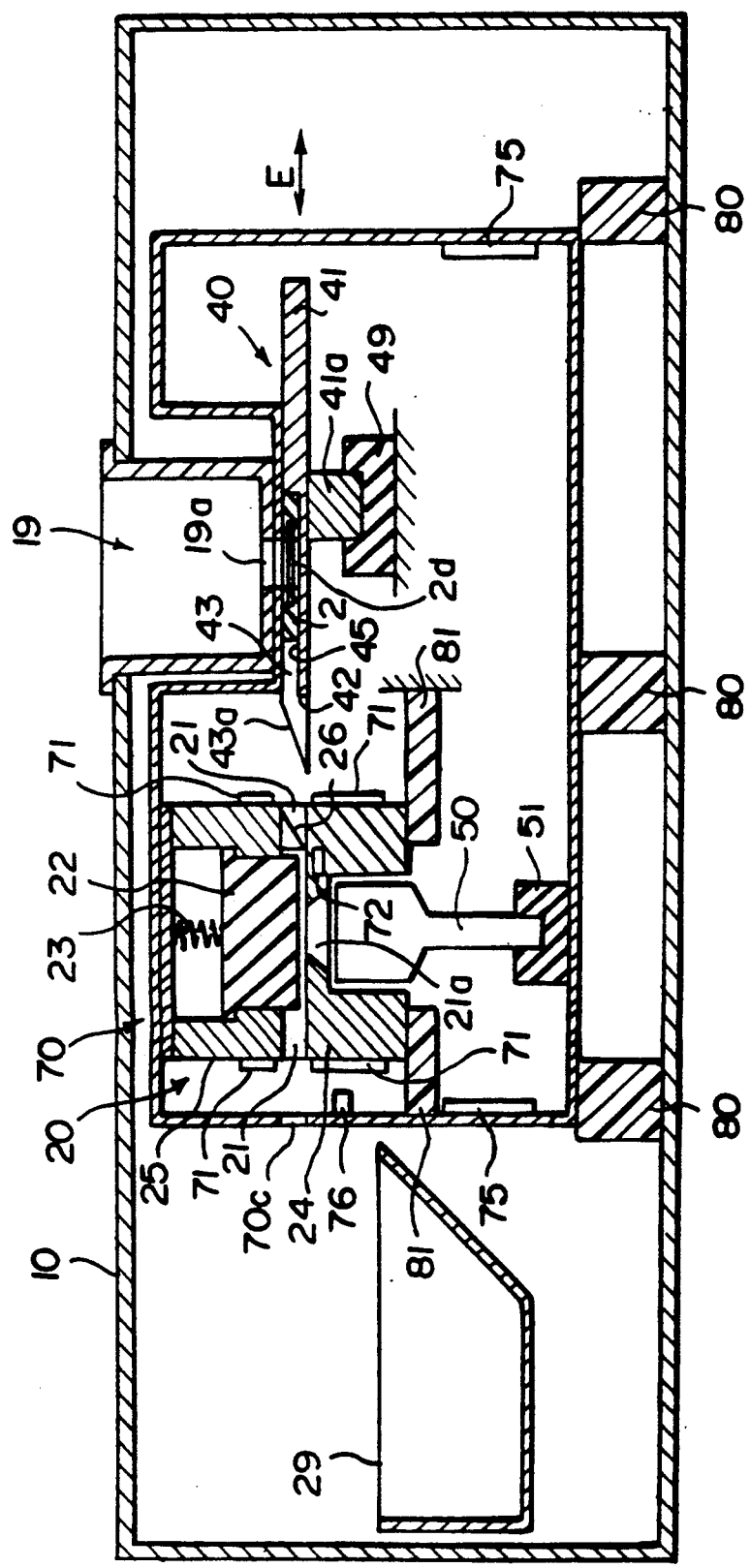
FIG. 6 is a sectional side view taken along line II—II of FIG. 4.

FIG. 3 is a perspective view showing an embodiment of the biochemical analysis apparatus in accordance with the present invention. FIG. 4 is a plan view showing the major part of the biochemical analysis apparatus shown in FIG. 3, with a housing thereof omitted. FIG. 5 is a sectional front view taken along line I—I of FIG. 4, and FIG. 6 is a sectional side view taken along line II—II of FIG. 4. The embodiment of the biochemical analysis apparatus in accordance with the present invention will hereinbelow be described with reference to FIGS. 3, 4, 5, and 6.

The chemical analysis apparatus is provided with a cartridge loading section 11 and a sample application device 30, which are disposed on a housing 10. In the cartridge loading section 11, a cartridge 3 is loaded in which a single correction slide 1 and a plurality of chemical analysis slides 2, 2, . . . are accommodated. The cartridge loading section 11 serves as an introducing section, from which the analysis media are introduced into the biochemical analysis apparatus. The sample application device 30 applies a droplet of a liquid sample to the film 2d of a chemical analysis slide 2. An incubator 20, which incubates a chemical analysis slide 2, is located inside of the housing 10. Also, a slide feed-in and ejection means 40, which moves a correction slide 1 and chemical analysis slides 2, 2, inserts them one after another into the incubator 20, and thereafter ejects them from the incubator 20 into a receiving member 29; is located inside of the housing 10. In this embodiment, the receiving member 29 serves as an ejecting section into which the analysis media are ejected from the biochemical analysis apparatus. The path, along which the correction slide 1 and the chemical analysis slides 2, 2, . . . are introduced one after another from the cartridge loading section 11 into the biochemical analysis apparatus and thereafter ejected into the receiving member 29, constitutes an example of the movement path specified in the present invention. Also, the biochemical analysis apparatus is provided with a display section 14, which displays measured values, or the like, and operating key section 15 which gives various instructions to the biochemical analysis apparatus. Additionally, the biochemical analysis apparatus is provided with a disk slot 13 into which a floppy disk carrying the information about the standard calibration curve, a floppy disk used to record the results of biochemical analyses, or the like are inserted. In FIGS. 4, 5, and 6, the display section 14, the operating key section 15, and the disk slot 13 are omitted. In this embodiment, the floppy disk, which is inserted into the disk slot 13 and on which information about the standard calibration curve is recorded, constitutes an example of the storage means which stores the information about a calibration curve.

The standard calibration curve is created by a manufacturer from standard slides (i.e. standard analysis media) and a standard biochemical analysis apparatus having the same functions as the illustrated biochemical analysis apparatus. The standard calibration curve is created in the manner described above.

As illustrated in FIG. 3, in the cartridge 3, the correction slide 1 is located at the bottom, and a plurality of chemical analysis slides 2, 2, . . . are stacked on the correction slide 1.

As shown in FIG. 4, the correction slide 1 and the chemical analysis slides 2, 2, . . . accommodated in the cartridge 3 are pushed out by a pushing lever 12 one by one, starting with the lowest slide, to the background density measuring section 16. When the correction slide 1 is thus pushed out, a bar code reader reads the bar code 1a therefrom. When a chemical analysis slide 2 is pushed out, the bar code reader 18 reads the bar code 2a therefrom. The bar code reader 18 is an example of the first reading means which reads the information recorded on the correction value recording medium. The bar code reader 18 also serves as a second reading means which reads the information recorded on an analysis medium.

After the bar code reader 18 has read the bar code 1a from the correction slide 1, the correction slide is moved along the movement path, along which the chemical analysis slides 2, 2, ... are moved, and is ejected into the receiving member. On the basis of the information read by the bar code reader 18, the correction slide 1 and the chemical analysis slides 2, 2, are discriminated from each other. When the correction slide 1 is moved along the movement path, application of a liquid sample thereto and incubation thereof are not carried out.

As illustrated in FIG. 5, the background density measuring section 16 is composed of a frame 16a provided with a measuring opening 16b at the bottom section, and a retaining member 16d urged downwardly by a spring 16c in the frame 16a. A compartment 16e which houses the chemical analysis slide 2 is formed between the upper surface of the bottom section of the frame 16a and the retaining member 16d. A white reference plate 17W and a black reference plate 17B, whose densities serve as reference values in measuring the reflection density of the chemical analysis slide 2, are located on the right side of the background density measuring section 16.

Also, the incubator 20 is located on the right side of the white reference plate 17W and the black reference plate 17B. A plurality of compartments 21, 21, which house the chemical analysis slides 2, 2, ..., are formed in the incubator 20 so that the chemical analysis slides 2, 2, ... stand side by side in a line on the same plane as the chemical analysis slide 2 which is positioned in the background density measuring section 16. The incubator 20 is housed in a temperature-controlled chamber 70. As shown in FIGS. 3 and 4, the receiving member 29 is located in front of the temperature-controlled chamber 70. The receiving member 29 receives chemical analysis slides 2, 2, ... which have been used for biochemical analysis and which are ejected from the compartments 21, 21, ... Also, as shown in FIG. 5, a probe 50 of a reflection densitometer, which measures the reflection density of the film 2d of a chemical analysis slide 2, is located below the incubator 20. The probe 50 can move in the transverse direction indicated by the arrow C so that it faces the lower surface of the incubator 20. In this embodiment, the reflection densitometer is employed as an example of the measurement means defined in the present invention. The probe 50 is combined with a rail 51, which is secured to an upper surface of a bottom plate of the temperature-controlled chamber 70. The probe 50 is moved by a drive means (not shown), such as a linear motor, in the direction indicated by the arrow C in order to measure reflection densities of the chemical analysis slides 2, 2, ... which are housed in the compartments 21, 21, ... of the incubator 20. The rail 51 extends up to the position below the background density measuring section 16. Therefore, the probe 50 can move up to the background density measuring section 16 in order to measure the reflection density of the film 2d of the chemical analysis slide 2, which is positioned at the background density measuring section 16, and the reflection densities of the white reference plate 17W and the black reference plate 17B.

As shown in FIG. 6, a plurality of first heaters 71, 71, ... are secured to the incubator 20 and located along the respective compartments 21, 21, ... Also, a first temperature sensor 72 is located in the incubator 20 at a position close to a compartment 21. The first temperature sensor 72 generates a temperature detection signal, which is used to control a current flowing through the first heaters 71, 71, ... so that the temperature in the incubator 20 is kept at a predetermined value T (for example, 37° C.).

Also, a plurality of second heaters 75, 75, ..., which heat air in the temperature-controlled chamber 70, and a second temperature sensor 76, which detects the temperature in the temperature-controlled chamber 70, are located in the temperature-controlled chamber 70. The second temperature sensor 76 generates a temperature detection signal, which is used to keep the temperature in the temperature-controlled chamber 70 at the aforesaid predetermined temperature T. Therefore, the temperature in the incubator is controlled more reliably.

The temperature-controlled chamber 70 is secured to the bottom surface of the housing 10 via heat insulating materials 80, 80, ... Also, the incubator 20 is supported in the temperature-controlled chamber 70 via heat insulating materials 81, 81, ...

As shown in FIG. 4, the slide feed-in and ejection means 40 is located at the rear of the incubator 20 so that it can move in the transverse direction indicated by the arrow A and along a rail 49, which is secured in the temperature-controlled chamber 70. The slide feed-in and ejection means 40 moves up to a position facing the background density measuring section 16 (i.e. the position indicated by the chained line X in FIG. 4) as well as to the position facing the incubator 20. The chemical analysis slide 2, which has been pushed by the pushing lever 12 out of the background density measuring section 16, is received by the slide feed-in and ejection means 40 which has moved to the position indicated by the chained line X. The slide feed-in and ejection means 40 and the pushing lever 12 constitute an example of the movement means defined in the present invention.

The sample application device 30 is located at the rear of the slide feed-in and ejection means 40. The sample application device 30 can move on a base plate 31 in the transverse direction indicated by the arrow A. In front of the sample application device 30, a sample base 34 is located which supports thereon sample tubes 36, 36, and application tips 35, 35, ... positioned in two lines in the transverse direction. A pipette 32 of the sample application device 30 can move vertically (i.e. in the direction indicated by the arrow D in FIG. 5) and forwardly and backwardly (i.e. in the direction indicated by the arrow B in FIG. 4) with respect to the base plate 31. One of the application tips 35, 35, ... is fitted to the lower edge of the pipette 32, and the pipette 32 draws a predetermined amount of a liquid sample from one of the sample tubes 36, 36, ... into the application tip 35 by suction. Thereafter, at a sample applying section 19 shown in FIG. 1, the pipette 32 applies the liquid sample to the film 2d of the chemical analysis slide 2 which is positioned on the slide feed-in and ejection means 40. Each time a different liquid sample is to be applied to a chemical analysis slide 2, a different application tip 35 is fitted to the lower edge of the pipette 32 and used to apply the liquid sample. Therefore, different liquid samples do not mix with each other.

Configurations of the slide feed-in and ejection means 40 and the incubator 20 will hereinbelow be described with reference to FIG. 6.

With reference to FIG. 6, the slide feed-in and ejection means 40 is composed of a supporting block 41a, which can move along the rail 49 in the transverse direction indicated by the arrow A in FIG. 4, and a supporting plate 41 located on the supporting block 41a. The supporting plate 41 is constituted of a holding portion 45, which receives and holds the chemical analysis slide 2 thereon, step-like portions 43, 43 formed at both ends of the holding portion 45, a pair of wedge-like insert portions 43a, 43a which are formed at the leading edges of the step-like portions 43, 43, and a slide ejecting protrusion 42 which is formed at the leading edge of the holding portion 45.

The incubator 20 is composed of a supporting member 24, which supports the chemical analysis slide 2 fed into the incubator 20 and which has a read-out opening 21a, and a pushing member 22, which faces the supporting member 24 and which can move vertically. The incubator 20 also comprises a spring 23 which urges the pushing member 22 downwardly, a main body member 25 which supports the pushing member 22 so that it can be moved, and a leaf-spring stop 26 which is secured to an inlet opening 21b (shown in FIG. 4) of each compartment 21.

In cases where a chemical analysis slide 2, whose reflection density has been measured with the probe 50, is housed and held in a compartment 21 and is to be ejected and a new chemical analysis slide 2 supported on the slide feed-in and ejection means 40 is to be inserted into the compartment 21, the slide feed-in and ejection means 40 and the incubator 20 operate in the manner described below.

The chemical analysis slide 2 located in the compartment 21 is gripped between the supporting member 24 and the pushing member 22 by the urging force of the spring 23. When the supporting plate 41 moves forwardly (i.e. leftwardly in FIG. 6), the wedge-like insert portion 43a first comes between the pushing member 22 and the supporting member 24, and pushes the pushing member 22 up in order to release the gripping force on the chemical analysis slide 2. Thereafter, the slide ejecting protrusion 42 comes into contact with the rear edge of the chemical analysis slide 2 located in the compartment 21, pushes the chemical analysis slide 2 forwardly, and ultimately ejects the chemical analysis slide 2 out of the compartment 21 into the receiving member 29 via an opening 70c of the temperature-controlled chamber 70. At this time, the new chemical analysis slide 2, which is held at the holding portion 45 of the supporting plate 41, is located at a predetermined position in the compartment 21, and the leaf-spring stop 26 enters a pair of recesses (not shown) formed at the rear edge of the holding portion 45 of the supporting plate 41. Thereafter, the supporting plate 41 returns backwardly. At this time, since the leaf-spring stop 26 is in contact with the rear edge face of the chemical analysis slide 2 and prevents the chemical analysis slide 2 from moving, the supporting plate 41 alone returns backwardly. As a result, the chemical analysis slide 2 remains in the compartment 21, and is gripped between the supporting member 24 and the pushing member 22.

The operations of the aforesaid embodiment will be described hereinbelow.

First, among the correction slide 1 and the chemical analysis slides 2, 2, . . . stacked in the cartridge 3 which has been loaded in the cartridge loading section 11, the correction slide 1 located at the bottom of the stack is pushed out by the pushing lever 12, and housed in the compartment 16e in the background density measuring section 16. At this time, the bar code 1a recorded on the correction slide 1 is read with the bar code reader 18. From the bar code 1a, it is recognized that the slide is not a chemical analysis slide 2, but is the correction slide 1. The correction slide 1 is pushed out of the background density measuring section 16 before a measurement of its background density is made and is located on the holding portion 45 of the slide feed-in and ejection means 40, which is located at the position indicated by the chained line X in FIG. 4.

Thereafter, the slide feed-in and ejection means 40 moves along the rail 49 up to the position indicated by the chained line Z in FIG. 4, and inserts the correction slide 1 into a compartment 21 in the manner described above. The slide feed-in and ejection means 40 then returns to the position indicated by the chained line X.

Thereafter, a chemical analysis slide 2, which is now located at the bottom of the stack in the cartridge 3, is pushed out by the pushing lever 12, and housed in the compartment 16e in the background density measuring section 16. At this time, the bar code 2a recorded on the chemical analysis slide 2 is read with the bar code reader 18. The lot number of the chemical analysis slide 2, which lot number is represented by the bar code 2a, is compared with the lot number which is represented by the bar code 1a read from the correction slide 1. When the two lot numbers coincide with each other, the normal-type operation is subsequently carried out, i.e. the background density of the chemical analysis slide 2 is measured in the manner described below. When the two lot numbers do no coincide with each other, the normal-type operation is not carried out; instead an alarm buzzer (not shown) is activated, and a warning is given on the display section 14 shown in FIG. 3.

In cases where the two lot numbers coincide with each other, the probe 50 moves to the position facing the measurement opening 16b of the background density measuring section 16, and measures the background density of the chemical analysis slide 2 to which no liquid sample has been applied. When the probe 50 thus moves, it stands facing the white reference plate 17W and the black reference plate 17B, and measures their reflection densities. The measured reflection densities of the white reference plate 17W and the black reference plate 17B are utilized as reference densities when the measurement of the reflection density of the chemical analysis slide 2 is made.

After the background density of the chemical analysis slide 2 is measured, the chemical analysis slide 2 is pushed by the pushing lever 12 out of the background density measuring section 16 onto the holding portion 45 of the slide feed-in and ejection means 40, which is waiting at the position indicated by the chained line X in FIG. 4.

Then, the slide feed-in and ejection means 40 moves rightwardly along the rail 49 up to the position indicated by the solid line Y in FIG. 4, and faces the pipette 32 of the sample application device 30. At this position, the liquid sample which is contained in the sample tube 36 is fed by the pipette 32 onto the film 2d of the chemical analysis slide 2, which is held on the slide feed-in and ejection means 40.

Thereafter, the slide feed-in and ejection means 40 moves along the rail 49 in the transverse direction indicated by the arrow A to the position facing the predetermined compartment 21 of the incubator 20, and feeds the chemical analysis slide 2 into the compartment 21 in the manner described above. As described above, the temperature in the compartment 21 of the incubator 20 is kept at the predetermined temperature T. Therefore, the chemical analysis slide 2 housed in the compartment 21 is incubated at the predetermined temperature T. After the chemical analysis slide 2 is incubated in the incubator 20, the probe 50, which has moved to the position below the compartment 21, irradiates light to the film 2d of the chemical analysis slide 2 through the read out opening 21a, and detects the amount of light reflected by the film 2d. In this manner, the reflection density of the film 2d of the chemical analysis slide 2 is measured, and the concentration of the specific biochemical substance contained in the liquid sample, which has been applied to the film 2d, is determined. When the measurement is finished, the slide feed-in and ejection means 40 ejects the chemical analysis slide 2 from the compartment 21 into the receiving member 29. The operations described above are repeated automatically and continuously in order that biochemical analyses may be carried out on many chemical analysis slides.

Figure 7:
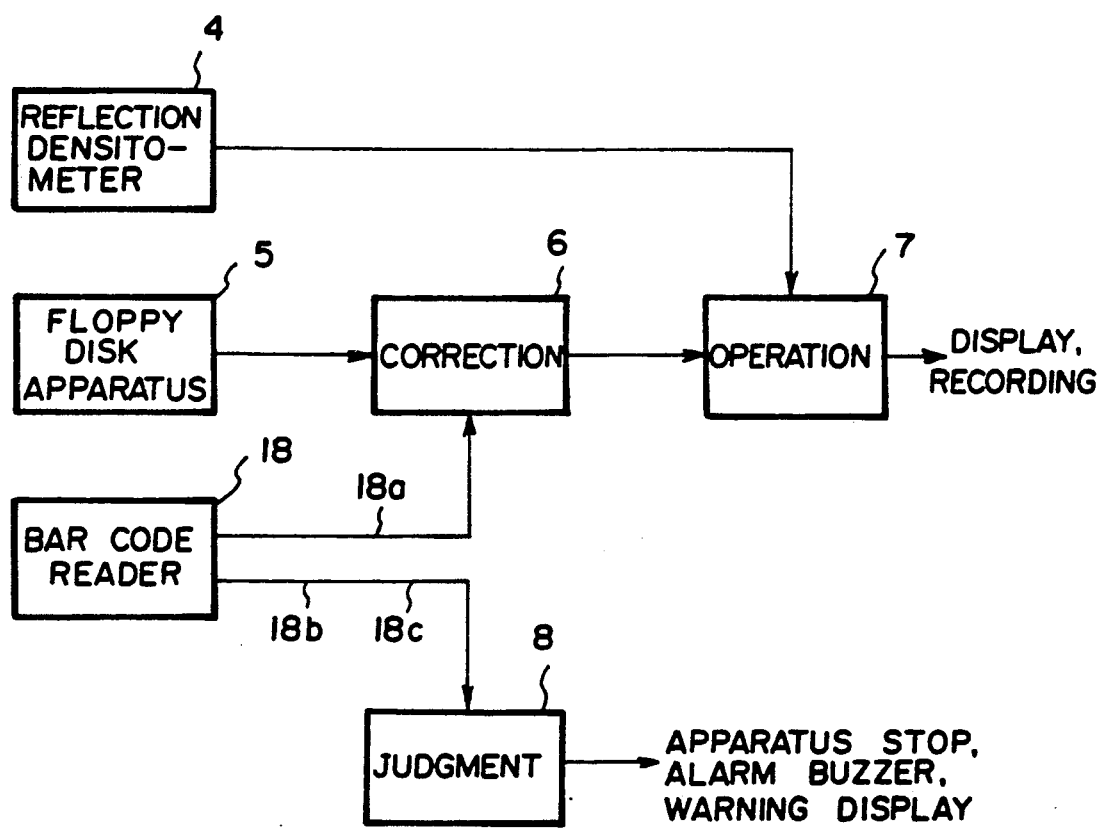
FIG. 7 is a block diagram showing how signals are processed in the biochemical analysis apparatus shown in FIG. 3.

How signals are processed in the aforesaid biochemical analysis apparatus will be described hereinbelow with reference to FIG. 7.

The bar code reader 18 reads the bar code 1a from the correction slide 1 and generates a signal 18a, which represents the correction values (i.e. the coefficients p and q), and a signal 18b, which represents the lot number of chemical analysis slides 2, 2, . . . corresponding to the correction slide 1. The signal 18a is fed into a correction means 6, and the signal 18b is fed into a judgment means 8. At this time, a signal representing a standard calibration curve is read from a floppy disk 5 and fed into the correction means 6.

Based on the correction values represented by the signal 18a, the correction means 6 corrects the standard calibration curve into a calibration curve suitable for the chemical analysis slides 2, 2, . . . which belong to the lot number corresponding to the correction slide 1. A signal representing the corrected calibration curve is fed into an operation means 7.

Thereafter, the bar code reader 18 reads the bar code 2a from the chemical analysis slide 2 and generates a signal 18c which represents the lot number of the chemical analysis slide 2. The signal 18c is fed into the judgment means 8. The judgment means 8 compares the lot number represented by the signal 18c and the lot number represented by the signal 18b. When the two lot numbers do not coincide with each other, the operation of the biochemical analysis apparatus is stopped. Also, an alarm buzzer (not shown) is activated, and a warning is given on the display section 14 shown in FIG. 3.

When the two lot numbers coincide with each other, the probe 50 of the reflection densitometer 4 is activated, and a measurement is made of the reflection densities of the white reference plate 17W and the black reference plate 17B, the background density of the chemical analysis slide 2 to which no liquid sample has been applied, and the reflection density of the chemical analysis slide 2 to which a liquid sample has been applied and which has undergone a color reaction. Signals representing these densities are fed into the operation means 7. From these densities, the operation means 7 accurately calculates the optical density, which depends on how much of a reaction product was formed by the reaction between the liquid sample and the reagent in the film 2d of the chemical analysis slide 2. Thereafter, the operation means 7 uses the corrected calibration curve in order to convert the calculated optical density into a concentration of the specific biochemical substance in the liquid sample. The concentration thus determined is displayed on the display section 14, or a signal representing the concentration is stored on a floppy disk.

In the aforesaid embodiment, the colorimetric or fluorometric biochemical analysis method and apparatus are used in order to measure the optical density which depends on how much of a reaction product was formed by the reaction between a liquid sample and a reagent in an analysis medium. The biochemical analysis apparatuses, the methods for correcting the results of biochemical analyses, and the correction value recording medium in accordance with the present invention are applicable also when an analysis medium provided with an electrochemical sensor is used in order to measure the current or the difference in potential which occurs across the electrochemical sensor.

We claim:

1. A biochemical analysis apparatus wherein liquid samples are independently applied to analysis media containing a reagent or an electrochemical sensor, which will interact with a specific biochemical substance contained in the liquid samples and give rise to changes in the analysis media, the changes which have occurred in the analysis media, the changes which have occurred curve, which represents the relationship between values thus measured and concentrations or activities of the specific biochemical substance in the liquid samples, is used to determine the concentrations or the activities of the specific biochemical substance from the values thus measured, wherein the improvement comprises:
i) a movement means which moves analysis media along a movement path connecting an introducing section, from which analysis media are introduced into said biochemical analysis apparatus, and an ejecting section into which analysis media, after they have been used in analyses, are ejected from said biochemical analysis apparatus,
ii) a measurement means for measuring changes, which have occurred in analysis media, while the analysis media are present in said movement path,
iii) a storage means which stores information about said calibration curve,
iv) a reading means for reading information about correction values, which are to be used to correct said calibration curve into a calibration curve suitable for analysis media used in the analyses, from a correction value recording medium used in the information about said correction values has been recorded,
v) a correction means for correcting said calibration curve, which is represented by the information read from said storage means, on the basis of said correction values which are represented by the information read from said correction value recording medium, and vi) an operation means which uses the corrected calibration curve to determine the concentration or the activity of the specific biochemical substances in a liquid sample from the value measured by said measurement means, wherein said reading means reads information about correction values from a correction value recording medium, which is shaped so that it is capable of being moved along said movement path in lieu of an analysis medium, while said correction value recording medium is present in said movement path.

2. A method for correcting the results of biochemical analyses wherein a variation in values obtained from biochemical analyses, which is caused by a difference in characteristics between a plurality of groups of analysis media, is eliminated in biochemical analyses in which liquid samples are independently applied to analysis media containing a reagent or an electrochemical sensor, which will interact with a specific biochemical substance contained in the liquid samples and give rise to changes in the analysis media, the changes which have occurred in the analysis media are measured, and thereafter a calibration curve, which represents the relationship between the values thus measured and concentrations or activities of the specific biochemical substance in the liquid samples, is used in order to determine the concentrations or the activities of the specific biochemical substance from the values thus measured, the method for correcting the results of biochemical analyses comprising the steps of:
i) creating a predetermined calibration curve which is used in the course of determining the concentrations or the activities of the specific biochemical substance in the liquid samples from biochemical analyses which are carried out with analysis media having predetermined characteristics,
ii) determining correction values for correcting said predetermined calibration curve in order to determine the concentrations or the activities of the specific biochemical substance in the liquid samples from biochemical analyses which are carried out with analysis media having different characteristics from said analysis media having predetermined characteristics,
iii) recording the information about said correction values on a correction value recording medium which is independent of the analysis media,
iv) storing the information about said predetermined calibration curve in said storage means of a biochemical analysis apparatus as defined in claim 1, and
v) in the course of using the biochemical analysis apparatus in order to determine the concentrations or the activities of the specific biochemical substance in the liquid samples, causing said reading means of the biochemical analysis apparatus to read the information about said correction values from said correction value recording medium.

3. A biochemical analysis apparatus wherein liquid samples are independently applied to analysis media containing a reagent or an electrochemical sensor, which will interact with a specific biochemical substance contained in the liquid samples and give rise to changes in the analysis media, the changes which have occurred in the analysis media are measured, and thereafter a calibration curve, which represents the relationship between values thus measured and concentrations or activities of the specific biochemical substance in the liquid samples, is used to determine the concentrations or the activities of the specific biochemical substance from the values thus measured, wherein the improvement comprises:
i) a movement means which moves analysis media along a movement path connecting an introducing section, from which analysis media are introduced into said biochemical analysis apparatus, and an ejecting section into which analysis media, after they have been used in analyses, are ejected from said biochemical analysis apparatus,
ii) a measurement means for measuring changes, which have occurred in analysis media, while the analysis media are present in said movement path,
iii) a storage means which stores information about said calibration curve,
iv) a reading means for reading information about correction values, which are to be used to correct said calibration curve into a calibration curve suitable for analysis media used in the analyses, from a correction value recording medium used in the information about said correction values has been recorded,
v) a correction means for correcting said calibration curve, which is represented by the information read from said storage means, on the basis of said correction values which are represented by the information read from said correction value recording medium, and
vi) an operation means which uses the corrected calibration curve to determine the concentration or the activity of the specific biochemical substances in a liquid sample from the value measured by said measurement means, wherein said reading means comprises a first reading means for reading information about correction values from a correction value recording medium and for reading information, which gives specifics about analysis media corresponding to a correction value recording medium and which is recorded on the correction value recording medium together with the information about correction values, a second reading means for reading information from the analysis media while they are present in said movement path, said information giving specifics about a correction value recording medium corresponding to analysis media and being recorded on the analysis media, and a judgment means for judging whether the information, which gives specifics about analysis media corresponding to a correction value recording medium and which has been read with first reading means, and the information, which gives specifics about a correction value recording medium corresponding to analysis media and which has been read with said second reading means, correspond or do not correspond to each other.

4. An apparatus as defined in claim 3 wherein said first reading means reads information about correction values and information, which give specifics about analysis media corresponding to a correction value recording medium, from a correction value recording medium, which is shaped so that it is capable of being moved along said movement path in lieu of an analysis medium, while said correction value recording medium is present in said movement path.

5. An apparatus as defined in claim 4 wherein said first reading means also serves as said second reading means and reads information, which gives specifics about a correction value recording medium corresponding to analysis media and which is recorded on the analysis media, from the analysis media while they are present in said movement path.

6. A method for correcting the results of biochemical analyses wherein a variation in values obtained from biochemical analyses, which is caused by a difference in characteristics between a plurality of groups of analysis media, is eliminated in biochemical analyses in which liquid samples are independently applied to analysis media containing a reagent or an electrochemical sensor, which will interact with a specific biochemical substance contained in the liquid samples and give rise to changes in the analysis media, the changes which have occurred in the analysis media are measured, and thereafter a calibration curve, which represents the relationship between the values thus measured and concentrations or activities of the specific biochemical substance in the liquid samples, is used in order to determine the concentrations or the activities of the specific biochemical substance from the values thus measured, the method for correcting the results of biochemical analyses comprising the steps of:

i) creating a predetermined calibration curve which is used in the course of determining the concentrations or the activities of the specific biochemical substance in the liquid samples from biochemical analyses which are carried out with analysis media having predetermined characteristics, ii) determining correction values for correcting said predetermined calibration curve in order to determine the concentrations or the activities of the specific biochemical substance in the liquid samples from biochemical analyses which are carried out with analysis media having different characteristics from said analysis media having predetermined characteristics, iii) recording the information about said correction values on a correction value recording medium which is independent of the analysis media, iv) recording the information, which gives specifics about a correction value recording medium corresponding to analysis media, on the analysis media, and recording the information, which gives specifics about analysis media corresponding to a correction value recording medium, on the correction value recording medium, storing the information about said predetermined calibration curve in said storage means of a biochemical analysis apparatus as defined in claims 3, 4, or 5, vi) causing said reading means of the biochemical analysis apparatus to read the information about said correction values and the information, which gives specifics about analysis media corresponding to a correction value recording medium, from said correction value recording medium, and vii) thereafter using the biochemical analysis apparatus in order to determine the concentrations or the activities of the specific biochemical substance in the liquid samples.

7. A correction value recording medium for use in a biochemical analysis apparatus as defined in claims 2, 4, or 5, the correction value recording medium being shaped so that it is capable of being moved along said movement path for analysis media in the biochemical analysis apparatus in lieu of an analysis medium.

* * * * *